United States Patent [19]

Chipens et al.

[11] 4,434,095
[45] Feb. 28, 1984

[54] CYCLIC ANALOGUE OF NATURALLY-OCCURRING PHAGOCYTOSIS-STIMULANT PEPTIDE - THREONYL-CYCLO-[-N$^\epsilon$-LYSYL-PROLYL-ARGINYL]

[75] Inventors: Gunar I. Chipens; Nadezhda I. Veretennikova; Zeltite A. Atare, all of Riga, U.S.S.R.

[73] Assignee: Institute Organicheskogo Sinteza, Riga, U.S.S.R.

[21] Appl. No.: 227,055

[22] PCT Filed: Apr. 2, 1980

[86] PCT No.: PCT/SU80/00060

§ 371 Date: Dec. 12, 1980

§ 102(e) Date: Dec. 12, 1980

[87] PCT Pub. No.: WO80/02141

PCT Pub. Date: Oct. 16, 1980

[30] Foreign Application Priority Data

Feb. 4, 1979 [SU] U.S.S.R. ............................... 2744960

[51] Int. Cl.$^3$ .......................................... C07C 103/52
[52] U.S. Cl. .............................................. 260/112.5 R
[58] Field of Search ................................. 260/112.5 R

[56] References Cited

U.S. PATENT DOCUMENTS 3,778,426 12/1973 Najjar ........................... 260/112.5 R

FOREIGN PATENT DOCUMENTS

WO80/02141 10/1980 PCT Int'l Appl. .......... 260/112.5 R

OTHER PUBLICATIONS

Munsgard et al., Internat'l Journal of Peptid and Protein Research, pp. 130–138.
Chem. Abstr. vol. 94, 1981, p. 114883m.

*Primary Examiner*—Delbert R. Phillips
*Attorney, Agent, or Firm*—Lilling & Greenspan

[57] ABSTRACT

A novel substance, that is a cyclic analogue of a naturally-occurring phagocytosis-stimulant peptide - threonyl-cyclo-[-N$^\epsilon$-lysyl-prolyl-arginyl-] of the formula:

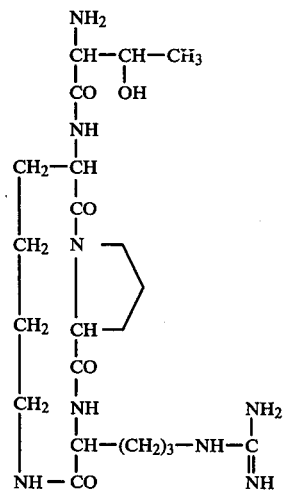

A method for preparing threonyl-cyclo-[-N$^\epsilon$-lysyl-prolyl-arginyl-] by way of a step-wise building-up of the peptide chain from the C-terminal by means of activated ethers of benzyloxycarbonyl-proline, tert-.butyloxycarbonyl- -N$^\epsilon$-benzyl-oxycarbonyl-lysine and tert.butyloxycarbonyl-threonine, followed by cyclization of the resulting partly blocked tetrapeptide using Woodward reagent in an excess of dimethylformamide and isolation of the desired product.

2 Claims, No Drawings

CYCLIC ANALOGUE OF NATURALLY-OCCURRING PHAGOCYTOSIS-STIMULANT PEPTIDE - THREONYL-CYCLO-[-N$^\epsilon$-LYSYL-PROLYL-ARGINYL]

FIELD OF THE INVENTION

The present invention relates to novel biologically active peptide-type compounds, namely to a novel cyclic analogue of a naturally-occurring phagocytosis-stimulant threonyl-cyclo-[-N$^\epsilon$-lysyl-prolyl-arginyl] possessing a phagocytosis-stimulating activity which is useful in medicine as an immunostimulant possessing a wide range of action and resistance against carboxypeptidases.

BACKGROUND OF THE INVENTION

Tuftsin having threonyl-cyclo-[-N$^\epsilon$-lysyl-prolyl-arginyl-] as its analogue comprises a fragment of a heavy chain of immunoglobulins, class IgG, of a human being (Thr-Lys-Pro-Aig). This tetrapeptide reveals a considerable stimulant effect with regard to various immunological responses in vivo and in vitro. It substantially increases phagocytic activity of leukocytes and macrophages, and activates immunogenesis of the latter, etc. (cf. Proc. Natl. Acad. Sci USA, vol. 75, No. 7, 1978; E. Tzehoval, S. Segal, Y. Stabinsky, M. Fridkin, Z. Spirer, M. Feldman "Tuftsin (an Ig-associated tetrapeptide) triggers the immunogenic function of macrophages: Application for activation of programmed cells", pp. 3400–3404).

It has been suggested that tuftsin is useful as a therapeutical remedy for the treatment of diseases associated with a lower activity of leukocytes, as well as splenectomy and certain spleen disturbances accompanied by a noticeably reduced resistance of the organism against infectious diseases. In such cases tuftsin can replace γ-globulin (J. Pediat. vol. 80, No. 4, 1972, D. Constantopoulos, V. D. Najjar, J. W. Smith "Tuftsin deficiency: a new syndrome with defective phagocytosis", pp. 464–572).

A disadvantage of tuftsin as a medicated compound resides in its rapid splitting by enzymes such as carboxypeptidases thus defining its short-time effect under in vivo conditions.

The cyclic analogue of the naturally-occurring phagocytosis-stimulant peptide—threonyl-cyclo-[-N$^\epsilon$-lysyl-prolyl-arginyl-] has not been hitherto described in the literature.

DISCLOSURE OF THE INVENTION

The present invention is directed to the provision of such a novel compound which would be resistant towards the enzymatic splitting agents such as carboxypeptidases.

This object is accomplished by a novel cyclic analogue of a naturally-occurring phagocytosis-stimulant peptide, viz. threonyl-cyclo-[-N$^\epsilon$-lysyl-prolyl-arginyl-] of the formula:

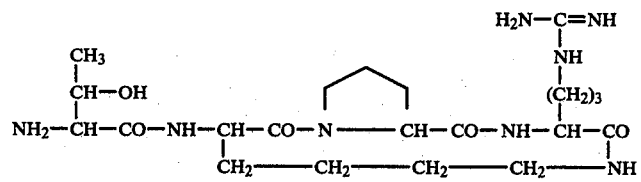

and by a method for preparing same by a step-wise building-up of the peptide chain from the C-terminal using activated ethers of benzyloxycarbonylproline, tert. butyloxycarbonyl-N$^\epsilon$-benzyloxycarbonyl-lysine and tert.butyloxycarbonylthreonine, followed by cyclization of the resulting partly blocked tetrapeptide by means of the Woodward reagent and isolation of the desired product.

BEST MODE FOR CARRYING-OUT THE INVENTION

According to the present invention the novel compound, viz. threonyl-cyclo-[-N$^\epsilon$-lysyl-prolyl-arginyl-] has the following formula:

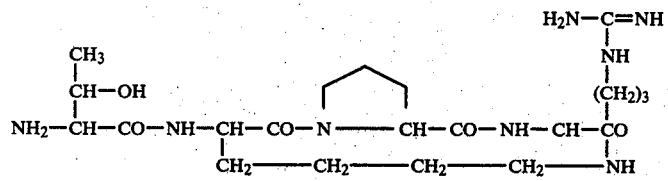

Cyclo-[-N$^\epsilon$-lysyl-prolyl-arginyl-] comprises an amorphous white powder decomposing above 100° C.; specific rotation $[Z]_D^{22} - 63°$ (c 0.2; 5% CH$_3$COOH).

Elemental analysis: Found, % by weight: C 40.18; H 7.47; N 14.68. Calculated, for C$_{21}$H$_{38}$N$_8$O$_5$.2CH$_3$COOH.4H$_2$O, % by weight: C 44.50; H 8.06; N 16.60.

Aminoacid analysis: Thr-1.0; Lys-1.1; Pro-0.9; Arg-1.0.

Electrophoretic analysis: electrophoretic mobility is determined through the ratio to histidine in 1 N acetic acid on paper FN-15 (GDR) at the voltage difference of 900 V. For the novel compound according to the present invention E$_{his}$=0.90 (pH 2.4).

Chromatographic analysis: chromatographic mobilities R$_f$=0.07 (n.butanol-ethanol-water-acetic acid-80:10:30:5), R$_f$=0.22 (n.butanol-pyridine-water-acetic acid 30:20:24:6) were determined on "Merck" plates.

Biological activity of threonyl-cyclo-[-N$^\epsilon$-lysyl-prolyl-arginyl-] is studied in vitro experiments. The effect of this compound on the phagocytic ability of rat's blood segmented neutrophils is studied in comparison with the effect of a known stimulant of phygocytosis-tuftsin (Thr. Lys. Pro. Arg. 2CH$_3$COOH.3H$_2$O) prepared in the Institute of Organic Synthesis Latv. SSR Academy of Sciences. The phagocytic ability of segmented neutrophils is determined following Gostev's procedure (cf. Proc. USSR Acad. Med. Sci., Nutrition Problems, "Role of Protein in Nutrition", vol. 13, iss. 2, 1950, Moscow; V. S. Gostev, M. N. Petriashina, S. A. Popovkina, A. K. Saakov "Phagocytosis, complement and blood coagulation with protein deficiency in food", pp. 110–116).

According to this procedure, rat's blood diluted with 2% sodium citrate in the ratio of 1:1 and solutions of the test compounds are employed. A one-day's age culture of coagulasopositive pathogenic strain *Staphylococcus aureus* in the concentration of 1 bin in 1 ml is added thereto. The mixture is incubated in a thermostat at 37° C. for 30 minutes. Then smears are prepared, fixed with methanol and dyed according to Romanovsky-Gymza. 100 segmented neutrophils are counted, the number of bacteria-absorbing is calculated among them (% of active phagocytes) and an average number of bacteria in one segmented neutrophil (phagocytic number). The phagocytic parameters are shown in the Table hereinbelow.

As seen from the Table, threonyl-cyclo-[-N$^\epsilon$-lysyl-prolyl-arginyl-] in concentrations of $3 \cdot 10^{-6}$ and $3 \cdot 10^{-7}$ M reveals a stimulant effect on phagocytic activity of leukocytes and shows no inhibiting effect relative to the action of tuftsin.

Preparation of threonyl-cyclo-[-N$^\epsilon$-lysyl-prolylarginyl-] is effected in the following manner.

p-Nitrophenyl ether of benzyloxycarbonylproline is reacted with arginine to give benzyloxycarbonyl-prolyl-arginine.

Then the thus-prepared compound is dissolved in glacial acetic acid, treated with a solution of hydrogen bromide in glacial acetic acid to obtain prolyl-arginine.

The prolyl-arginine obtained in the previous stage is then reacted with pentafluorophenyl ether of tert.butyloxycarbonyl-benzyloxycarbonyl-lysine with the formation of tert. butyloxycarbonyl-N$^\epsilon$-benzyloxycarbonyl-lysyl-prolyl-arginine which is treated with a 70% aqueous solution of trifluoroacetic acid to give N$^\epsilon$-benzyloxycarbonyl-lysyl-prolyl-arginine. Then the reaction of interaction between pentafluorophenyl ether of tert.butyloxycarbonyl-threonine and N$^\epsilon$-benzyloxycarbonyl-lysyl-prolyl-arginine occurs, with the formation of tert.butyloxycarbonyl-threonyl-N$^\epsilon$-benzyloxycarbonyl-lysyl-prolyl-arginine. The thus-obtained product is hydrogenated to form tert.butyloxycarbonyl-threonyl-lysyl-prolyl-arginine.

Tert.butyloxycarbonyl-threonyl-lysyl-prolyl-arginine is cyclized to give tert.butyloxycarbonyl-threonyl-cyclo-[N$^\epsilon$-lysyl-prolyl-arginyl-]. The resulting product is treated with a solution of hydrogen chloride in glacial acetic acid for the preparation of threonyl-cyclo-[-N$^\epsilon$-lysyl-prolyl-arginyl-].

The general scheme of the synthesis is shown in the following FIGURE.

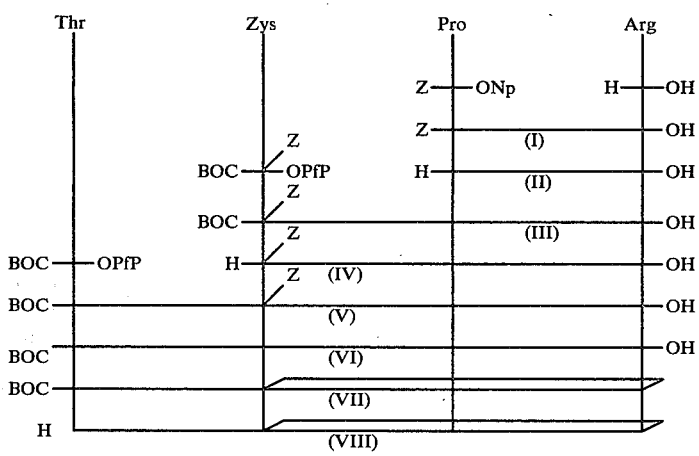

The novel analogue of tuftsin-threonyl-cyclo-[-N$^\epsilon$-lysyl-prolyl-arginyl-] retains a high level of phagocytosis-stimulating activity relative to segmented neutrophils of rat blood in vitro characteristic of tuftsin, but unlike the latter it is resistant against enzymatic hydrolysis by means of carboxypeptidases.

| | 1 | 2 | 3 | 4 |
|---|---|---|---|---|
| Inhibition in respect of the effect of tuftsin, $\dfrac{P_t - P}{P_t - P_c} \cdot 100\%$ | — | — | — | |
| Threonyl-cyclo-[—N$^\epsilon$—lysyl-prolyl-arginyl—] concentration | | $3 \cdot 10^{-6}$ M | | $3 \cdot 10^{-7}$ M |
| | | 3.64 | | 3.40 |
| | | 75.5 | | 82.0 |
| | | 14.3 | | −55.8 |

$P_t$ - number of active phagocytes upon the effect of tuftsin;
$P_c$ - number of active phagocytes in the control;
$P_e$ - number of active phagocytes upon tthe effect of the preparation according to the present invention and tuftsin.

For a better understanding of the present invention the following example illustrating the same is given hereinbelow.

For the synthesis of threonyl-cyclo-[-N$^\epsilon$-lysyl-prolyl-arginyl-] use is made of aminoacids and derivatives thereof available from "Reakal" company, Hungary. All the aminoacids have the L-configuration. Melting points determined in open capillaries are given without corrections. Homogeneity of the resulting compounds is checked on plates "Silufol W-254", "Eastman", "Merck". Also shown are chromatographic mobility values $R_f$ in the following systems: A—n-butanol-ethanol-water-acetic acid (80:10:30:5); B—n-butanol-pyridine-water-acetic acid (30:20:24:6), as well as electrophoretic mobility relative to histidine ($E_{his}$) on paper FN-15 (GDR) in 1 N (pH 2.4) and 5 N (pH 1.4) acetic acid. Rotation angles are determined on a polarimeter

I. BENZYLOXYCARBONYL-PROLYL-ARGININE

To a solution of 37 g (0.1 mol) of p-nitrophenyl ether of benzyloxycarbonylproline in 360 ml of dioxane there is added a solution of 16 g (0.09 mole) of arginine in 160 ml of water under vigorous stirring. After two hours the solvent is evaporated and the residue is dissolved in 100 ml of dimethylformamide. The solution is stirred at room temperature (25° C.) for 72 hours and then poured into 1 liter of ethylacetate. After residence of the reaction mixture for 12 hours in a cooler the resulting precipitate is filtered-off, washed on the filter with ethylacetate and diethyl ether. After recrystallization of the product from a mixture of ethanol-diethyl ether (1:5) there are obtained 35 g (96%) of benzyloxycarbonyl-prolyl-arginine having the following properties: melting point 137°–140° C., $[L]_D^{20} -46.6°$ (c 1.0; $H_2O$); $R_f$ 0.53 (A, "Eastman"); 0.66 (B, "Eastman"), $E_{his}$ 0.56 (pH 2.4).

Found, % by weight: C 53.17; H 6.08; N 15.91. Calculated for $C_{19}H_{27}N_5O_5.H_2O$, % by weight: C 56.28; H 6.71; N 17.27.

II. PROLYL-ARGININE

It is produced by treating compound I with 1 N hydrogen bromide in glacial acetic acid. The solution of the hydrogen-bromide salt of prolyl-arginine II in 500 ml of water is treated with an anionite to the negative reaction on Br−ions. The yield of prolyl-arginine is 23 g (quantitative).

III. TERT.BUTYLOXYCARBONYL-N$^\epsilon$-BENZYLOXYCARBONYL-LYSYL-PROLYL-ARGININE To a solution of 53 g (0.1 mol) of pentafluorophenyl ether of tert.butyloxycarbonyl-N$^\epsilon$-benzyloxycarbonyl-lysine in 300 ml of dioxane there is added, under vigorous stirring, a solution of 23 g (0.08 mol) of prolyl-arginine II in 100 ml of water. After two hours the solvent is evaporated and the residue is dissolved in 150 ml of dimethylformamide. The solution is stirred for 48 hours at room temperature (25° C.), dimethylformamide is distilled-off to ⅓ volume, whereafter the reaction mixture is poured into 1 liter of diethyl ether. A further treatment is effected as described in the case of compound I. After recrystallization of the product from a mixture of ethylacetate-ethanol-diethyl ether (3:1:30) there are obtained 47 g (75%) of tert.butyloxycarbonyl-N$^\epsilon$-benzyloxycarbonyl-lysyl-prolyl-arginine having the following properties: M.p. 90° C., $[L]_D^{20} -39°$ (c 1.0; 10% $CH_3COOH$); $R_f$=0.51/A, "Eastman"/, 0.82/B, "Eastman"/; $E_{his}$=0.34 (pH 2.4).

Found, % by weight: C 54.66; H 7.98; N 15.89. Calculated for $C_{30}H_{47}N_7O_8$, % by weight: C 56.86; H 7.48; N 15.47.

IV. N$^\epsilon$-BENZYLOXYCARBONYL-LYSYL-PROLYL-ARGININE

This compound is produced by treating compound III with 70% aqueous solution of trifluoroacetic acid and an anionite to remove trifluoroacetate. The yield of the desired product is 11 g (quantitative).

V. TERT.BUTYLOXYCARBONYL-THREONYL-N$^\epsilon$-BENZYLOXYCARBONYL-LYSYL-PROLYL-ARGININE 2.18 g (4.1 mmol) of N$^\epsilon$-benzyloxycarbonyl-lysyl-prolyl-arginine IV in 30 ml of water are added, under stirring, to a solution of 2.10 g (5.3 mmol) of pentafluorophenyl ether of tert.butyloxycarbonyl-threonine in 70 ml of dioxane. Then the reaction mixture is treated following the procedure described for the synthesis of compound III. The yield of the desired product—tert.butyloxycarbonyl-threonyl-N$^\epsilon$-benzyloxycarbonyl-lysyl-prolyl-arginine is 2.65 g (188%).

The resulting compound V is purified on a column (3×100) with silica gel ("Chemapol" CSSR, L 40/100μ) in system A. The collected fractions are controlled by TLC techniques. The fractions with $R_f$=0.45 (A, "Silufol") are combined. The yield of the product (V) is 180 g (60%). The thus-prepared compound has the following properties: M.p. 175° C.; $[L]_D^{20} -64.6°$ (c 1.0; $H_2O$); $R_f$==0.65 (B, "Merck"); $E_{his}$ 0.41 (pH 1.4).

Found, % by weight: C 52.44; H 7.26; N 14.42. Calculated for $C_{34}H_{55}N_8O_{10}.2H_2O$, % by weight: C 52.98; H 7.59; N 14.54.

VI. TERT.BUTYLOXYCARBONYL-THREONYL-LYSYL-PROLYL-ARGININE 1.23 g (1.67 mol) of tert.butyloxycarbonyl-threonyl-N$^\epsilon$-benzyloxycarbonyl-lysyl-prolyl-arginine (V) is hydrogenated under atmospheric pressure in the presence of palladium black in a solution of 20 ml of methanol for 10 hours. Thereafter the solution is filtered, evaporated to dryness and rubbed under dry diethyl ether. The resulting substance is dried over phosphorus pentoxide in vacuum under a residual pressure of 1 mm Hg.

The yield of tert.butyloxycarbonyl-threonyl-lysyl-prolyl-arginine is 1.05 g (99%); the product has the following properties: M.p. 170° C.; $[L]_D^{20} -66°$ (c 1.0; $H_2O$); $R_f$=0.05 (A, "Silufol"); 0.16 (A, "Merck"); $E_{his}$=0.84 (pH 1.4). Found, % by weight: C 49.26; H 8.30; N 16.82. Calculated for $C_{26}H_{50}N_8O_8.CH_3COOH.H_2O$, % by weight: C 49.48; H 8.35; N 16.58.

VII. TERT.BUTYLOXYCARBONYL-THREONYL-CYCLO-[N$^\epsilon$-LYSYL-PROLYL-ARGINYL-]

0.85 g (1.34 mmol) of tert.butyloxycarbonyl-threonyl-lysyl-prolyl-arginine (VI) is dissolved, under stirring, in 260 ml of dimethylformamide, the solution is cooled to 0° C. and a solution of 1.86 ml (1.34 mmol) of triethylamine in 200 ml of dimethylformamide is dropwise added thereto for one hour. Afterwards, while maintaining the solution temperature at 0° C., a suspension of 0.33 g (1.34 mmol) of Woodward reagent (N-ethyl-5-phenylisooxazolium-3'-sulphonate) in 150 ml of dimethylformamide is drop-wise added for 2 hours and cooling is continued for an additional 30 minutes. Then the reaction mixture is stirred at room temperature for 170 hours. The solvent is evaporated, the residue is treated with dry ether, filtered-off and dried under 1 mm Hg. The yield is 1.18 g (mixture of the starting product, formed substance and Woodward reagent). After purification in a column (3×100) with silica gel ("Chemapol", CSSR, L 40/100μ) in system A fractions with $R_f$=0.34 (A, "Merck") are collected to give 0.17 g (20%) of tert.butyloxycarbonyl-threonyl-cyclo-[-N$^\epsilon$- lysyl-prolyl-arginyl-] having the following properties: $[L]_D^{20} - 46.6°$ C. (c 0.03; MeOH); $R_f = 0.73$ (B, "Merck"); $E_{his} = 0.38$ (pH 2.4).

Found, % by weight: C 46.93; H 7.03; N 13.70. Calculated for $C_{26}H_{46}N_8O_7 \cdot 2CH_3COOH \cdot 2H_2O$, % by weight: C 48.77; H 7.91; N 15.16.

VIII. THREONYL-CYCLO-[-N$^\epsilon$-LYSYL-PROLYL-ARGINYL-]

0.13 g (0.21 mmol) of tert.butyloxycarbonyl-cyclo-[-N$^\epsilon$-lysyl-prolyl-arginyl-] VII are dissolved in 5 ml of lacial acetic acid and treated with 0.5 ml of 9.2 N hydrogen chloride in dioxane. 20 minutes thereafter the solvent is evaporated, the residue is treated with dry diethyl ether, dried under 1 mm Hg over caustic potassium. The product is purified in a column with CM-cellulose (Whatman CM-32) at a gradient of ammonium acetate of from 0.01 M (pH 4.5) to 0.25 M (pH 6.5).

The yield of pure threonyl-cyclo-[-N$^\epsilon$-lysyl-prolyl-arginyl-] is 0.03 g (23%), the compound has the following properties: $[L]_D^{20} = -63°$ (c 0.2; 5% CH$_3$COOH); $R_f = =0.07$ (A, "Merck"), 0.22 (B, "Merck"); $E_{his} = 0.9$ (pH 2.4). Found, % by weight: C 40.18; H 7.47; N 14.68. Calculated for $C_{21}H_{38}N_8O_5 \cdot 2CH_3COOH \cdot 4H_2O$, % by weight: C 44.50; H 8.06; N 16.60.

Hydrolysis of threonyl-cyclo-[-N$^\epsilon$-lysyl-prolyl-arginine-] (VIII) with carboxypeptidase B under optimal conditions has proved resistance of the C-terminal arginine against splitting in contrast to tuftsin.

INDUSTRIAL APPLICABILITY

Threonyl-cyclo-[-N$^\epsilon$-lysyl-prolyl-arginyl-] can be useful in medicine as an immunostimulant having a wide range of action and resistance to enzymatic splitting under in vivo conditions. This enables its application as a pharmaceutical agent per os.

We claim:

1. A cyclic analogue of a naturally-occurring phagocytosis-stimulant peptide—threonyl-cyclo-[-N$^\epsilon$-lysyl-prolyl-arginyl-] of the formula:

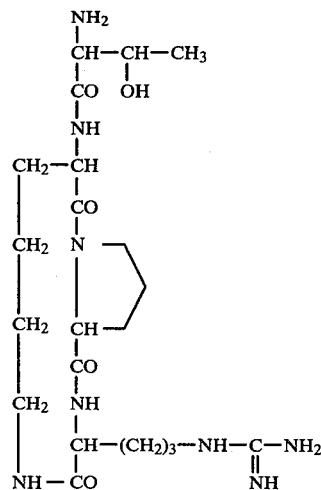

2. A method for preparing threonyl-cyclo-[-N$^\epsilon$-lysyl-prolyl-arginyl-] according to claim 1, wherein the synthesis of threonyl-cyclo-[-N$^\epsilon$-lysyl-prolyl-arginyl-] is effected by way of a step-wise building-up of the peptide chain from the C-terminal using activated ethers of benzyloxycarbonyl-proline, tert.butyloxycarbonyl-N$^\epsilon$-benzyloxycarbonyl-lysine and tert.butyloxycarbonyyl-threonine, followed by cyclization of the resulting partly blocked tetrapeptide by means of Woodward reagent in an excess of dimethylformamide and isolation of the desired product.

* * * * *